US005589475A

United States Patent [19]
Snorrason

[11] Patent Number: 5,589,475
[45] Date of Patent: Dec. 31, 1996

[54] BENZODIAZEPINE TREATMENT

[76] Inventor: Ernir Snorrason, Stigahlid 80, 105 Reykjavík, Iceland

[21] Appl. No.: 292,230

[22] Filed: Aug. 22, 1994

Related U.S. Application Data

[63] Continuation of Ser. No. 883,037, May 14, 1992, abandoned.

[30] Foreign Application Priority Data

May 14, 1991 [IS] Iceland .......................................... 3706
Feb. 13, 1992 [DK] Denmark ..................................... 182/92

[51] Int. Cl.⁶ .................................................. A01N 43/46
[52] U.S. Cl. ............................................................ 514/215
[58] Field of Search ............................................. 514/215

[56] References Cited

PUBLICATIONS

CA 112: 48617 1989.
Medline 85: 195065 1985.
CA 110: 51228 1988.
Chemical Abstracts 92:121768q (1980).
Chemical Abstracts 101:16845u (1984).
Foster, et al. "Physostigimine Reversal Of Diazepam–Induced Depression," *Anethesia and Analgasia* 56(3): 348–352 (May–Jun. 1977).
Vateshsky, et al. "Mechanism Of Antagonism By Physostigimine Of Acute Flunitrazepam Intoxication," *Anesthesiology* 64(2): 248–252 (1986).
Blitt, et al. "Reversal Of Lorzaepam Delirium By Physostigmine," *Anesthesia and Analgesia* 54(5): 607–608 (Sep. Oct. 1975).
Lauven, et al. "Flumazenil (Ro 15–1788) and Physostigmine," *Resuscitation* 16/suppl., 542–548 (1988).
Hoffman, et al. "Cerebrovascular and Cerebral Metabolic Effects of Physostigmine, Midazolam, and a Benzodiazepine Antagonist," *Anesthesia and Analgesia* 65(6): 639–644 (Jun. 1986).
Pandit, et al. "Physostigmine Fails To Reverse Clinical Psychomotor, or EEG Effects Of Lorazepam," *Anesthesia and Analgesia* 62(7): 79–685 (Jul. 1983).
Deutsch, et al. "Acetylcholinesterase Activity in CSF in Schizophrenia, Depression, Alzheimer's Disease, and Normals," *Biological Psychiatry* 18(12): 1363–13763 (Dec. 1983).

*Primary Examiner*—Paul J. Killos
*Attorney, Agent, or Firm*—Foley & Lardner

[57] ABSTRACT

The use of a pharmaceutically acceptable cholinesterase inhibitor or a prodrug therefor for counteracting the sedative, hypnotic or respiratory depressive effects of benzodiazepines, substantially without interfering with the anxiolytic, antipsychotic, anticonvulsant, and muscle relaxant activity of benzodiazepines. When benzodiazepines are used for treatment of diseases where the sedative, hypnotic or respiratory depressive effects are undesirable, such as diseases selected from the group consisting of anxiety, anxiety neurosis, anxiety reactions, panic reactions, schizophrenia, affective or schizoaffective type schizophrenia, borderline psychosis, agitating endogene depressions, hyperactivity in children, and muscle spasms, the cholinesterase inhibitor of the present invention is particularly effective. The invention also is directed to use a pharmaceutically acceptable cholinesterase inhibitor or a prodrug therefor for the treatment of schizophrenia, in particular affective or schizoaffective type schizophrenia. The acetyl cholinesterase is preferably one that acts substantially selectively at nicotinic receptor sites, and which has selectively for acetyl cholinesterase opposed to butyryl cholinesterase, e.g., galanthamine or a galanthamine derivative.

42 Claims, 2 Drawing Sheets

BENZODIAZEPINE TREATMENT

This application is a continuation of Ser. No. 07/883,037, filed May 14, 1992 now abondoned.

SUMMARY OF THE INVENTION

The present invention relates to the use of cholinesterase inhibitors, such as galanthamine, for the preparation of a pharamceutical composition for counteracting the sedative or hypnotic or respiratory depressive effects of benzodiazepines, substantially without interfering with the anxiolytic, antipsychotic, anticonvulsant, and muscle relaxant activity of benzodiazepines.

Expressed in another manner, the invention relates to a method for counteracting the sedative, hypnotic or respiratory depressive effects of benzodiazepines, substantially without interfering with the above-mentioned anxiolytic and other desired properties of benzodiazepines, comprising administering, to a patient in subjected to benzodiazepine therapy, that is, a patient who receives benzodiazepine, an effective amount of a pharmaceutically acceptable cholinesterase inhibitor.

An aspect of the invention relates to the treatment of schizophrenia, in particular affective or schizoaffective type of schizophrenia, by administering, to a patient suffering from such a condition, an effective amount of a cholinesterase inhibitor, such as galanthamine.

GENERAL BACKGROUND

Benzodiazepines have been used for several decades, but have become increasingly popular because of their effects and their low toxicity compared to other drugs of similar actions.

The major known effects of benzodiazepines are anticonvulsant muscle relaxing sedative hypnotic anxiolytic antipsychotic.

Thus, the benzodiazepines are relevant as drugs in connection with a broad spectrum of diseases.

The mechanism of effect of the benzodiazepine drugs are unknown, but is believed to be an effect on the GABA-system of the central nervous system. However, the effect of the benzodiazepines seems to be some kind of an overall unspecific inhibition of the central nervous system independent of the transmitter in the regions affected.

When using benzodiazepines, some of their effects are desirable, but other may be considered as side effects with respect to the specific disease treated.

When any of the anticonvulsant, the muscle relaxing, the anxiolytic or the antipsychotic effects are desired, it is often a problem that the sedative and hypnotic effects of benzodiazepines prohibit the use of high dosages of benzodiazepines, or, when such high dosages are nevertheless necessary to get a reasonable effect of the treatment, make it necessary to hospitalize the patient. Even in the dosages used, e.g. against anxiety, the sedative effect of benzodiazepines may be disadvantageous.

DETAILED DISCLOSURE OF THE INVENTION

According to the invention, it has been surprisingly been found that a cholinesterase inhibitor counteracts the typical sedative and the hypnotic effects of benzodiazepines.

Thus, by administering, in accordance with the principle of the present invention, cholinesterase inhibitors to patients treated with benzodiazepines, it will be possible, because of the counteraction of the sedative and hypnotic effects, to use effective dosages of the benzodiazepines even where high dosages are necessary to obtain an effect, without disabling the patients from living a normal daily life.

The patients may be treated with amounts of benzodiazepine which are sufficient with respect to the desired effect on their condition, such amounts being established, e.g., in accordance with normal principles in benzodiazepine therapy, that is, by monitoring the symptoms of the disease to be treated and thereby establish an individual dosage which is effective. However, due to the use, according to the invention, of a cholinesterase inhibitor to counteract the sedative or hypnotic effects, the limitation on the dosages previously imposed due to these effects, is no longer necessary, and thus, a more efficient treatment with the benzodiazepines is obtained.

The dosage of the cholinesterase inhibitor, such as galanthamine, which will be effective to avoid the undesired sedative or hypnotic effect of the benzodiazepine in each particular case, can suitably be found by monitoring each patient individually, or may be assessed on the basis of experience gained. A more detailed discussion of suitable dosage ranges is given in the following.

In the present context, the term "a benzodiazepine" or "benzodiazepines" designate benzodiazepine as well as derivatives thereof which are normally classified as benzodiazepines in pharmaceutical textbooks such as, e.g., Ernst Mutschler, Arzneimittelwirkungen, Lehrbuch der Pharmaceutical makologie and Toxikologie, Aug. 5, 1986, Wissenschaftliche Verlagsgasellschaft mbk, Stuttgart, including, e.g., diazepam, dipotassiumchlorazepate, chlorasepate, chlor diazapid, medazepam, flurasepam, clobasam, clonasepam, nitrasepam, flunitrasepam, astazolam, bromazepam, alprazolam, lorazepam, lormetasepam, oxazepam, temazepam, brotizolam, triazolam, chlordiazepam, halazepam, or prazepam.

Some benzodiazepines are mostly used for their sedative or hypnotic effect; these benzodiazepines are typically those having a short half life. Other benzodiazepines are used for the other effects where the sedative or the hypnotic effects are considered undesirable or even side effects of the benzodiazepine. These benzodiazepines are, e.g., diazepam, dipotassiumchlorazepate, chlorazepate, chlordiazepid, medazepam, clobazam, clonazepam, estazolam, bromasepam, alprazolam, lorazepam, lormetazepam, oxazepam, brotizolam, chlordiazepam, halazepam, or prazepam.

The diseases treated with benzodiazepines constitute a broad spectrum of diseases because of the many effects of the benzodiazepines. Diseases where the sedative or hypnotic effects of the benzodiazepines are undesirable are diseases in connection with which the principle of the present invention is particularly important. Especially the treatment of the following diseases: anxiety, anxiety neurosis, anxiety reactions, panic reactions, schizophrenia, affective type schizophrenia, borderline psychosis, agitated endogenous depressions, hyperactivity in children, and muscle spasms, may benefit from the use of both a benzodiazepine and a cholinesterase inhibitor in accordance with the principle of the invention, as these diseases are known to require high dosages of benzodiazepine in order to obtain the benefit of the benzodiazepine therapy, the high dosages, on the other hand, incurring the above-mentioned severe disadvantages due to the sedative and hypnotic effects if no administration of cholinesterase inhibitor is performed in connection with the benzodiazepine treatment.

The cholinesterase inhibitor may be administered simultaneously with the benzodiazepine, either as separate products or from a combined product containing both the benzodiazepine and the cholinesterase inhibitor; the combined product, on its side, may contain the cholinesterase inhibitor and the benzodiazepine either as separate dosage forms in a kit product, or as one combined dosage form containing both the cholinesterase inhibitor and the benzodiazepine.

The cholinesterase inhibitor will not necessarily be given at the same time as the benzodiazepine. Thus, e.g., if, after some time of administration of a benzodiazepine as the sole or main medication, the sedative or hypnotic effects of the benzodiazepine has become a clinical problem, a cholinesterase may be administered to counteract the sedative or hypnotic effects either in addition to the benzodiazepine or alone if the treatment with benzodiazepine has been stopped temporarily. From this it will be understood that the cholinesterase may also be used in the treatment of sedative or the hypnotic effects resulting from an overdose of benzodiazepine.

Schizophrenia and affective type schizophrenia, and schizo- affective type of schizophrenia are conditions in which benzodiazepine therapy, such as treatment with clonazepam, is important, confer the above discussion. However, according to the present invention these conditions may also be treated with a cholinesterase inhibitor alone, or with a cholinesterase inhibitor as the main functional drug with respect to the treatment of the schizophrenia in question.

In the treatment of the above-mentioned types of schizophrenia, the cholinesterase inhibitor may, according to the present invention, be used as the sole or main drug in the treatment of not only the apatho-abulic manifestations of the schizophrenia but also for other manifestations, especially for the affective type schizophrenia. This is important to note in view of the fact that Vovin et al. (Correction of apathetic-abulic manifestations of schizophrenia with cholinotropic drugs, Zhurnal Nevropatol Psikhiatr. 1991(s), 111–115) disclose the use of galanthamine or desoxypeganin together with benactizin for the treatment of the apatho-abulic manifestations of schizophrenia; the paper contains no indication of the use of galanthamine or any other cholinesterase alone or as the main drug.

Compounds which function as cholinesterase inhibitors may be divided into several groups, namely poison gases for use in warfare, insecticides, such as malathion, and drugs. In the present context, the term "pharmaceutically acceptable" indicates that the cholinesterase inhibitors in question are not such which will be poisonous, in other words, they pertain to the drug group and not to the poison group.

Pharmaceutically acceptable cholinesterase inhibitors are, e.g., physostigmine, tacrine and tacrine analogues, galanthamine, epigalanthamine, norgalnthamine, fasciculin, metrifonate, heptyl-physostigmine, norpyridostigmine, norneostigmine, and huperzine. Some of the cholinesterase inhibitors show certain undesirable properties, such as short half life, etc. In some cases, such deficiencies can be compensated for by modifying the compound into a prodrug for the active compound, in accordance with well-known principles for prodrug construction, such as introduction of hydrophilic groups to enhance the solubility of a compound in water, thus making it possible to formulate the compound as a an injection solution, an introduction of lipophilic groups such as estar groups to enhance the capability of the compound to pass the blood-brain barrier.

The presently preferred cholinesterase inhibitor used according to the invention is galanthamine. Galanthamine is known as an acetylcholinesterase inhibitor acting substantially only at nicotinic receptor sites, that is, having a high selectivity for acetylcholinesterase as opposed to butyrylcho- linestarase. A more detailed discussion of galanthamine and galanthamine derivatives is given below:

Galanthamine is a well-known acetylcholinesterase inhibitor which is active substantially selectively at nicotinic receptor sites and has substantially no effect on muscarinic receptor sides, is capable of passing the blood-brain barrier in humans, and presents no severe side effects in therapeutically necessary dosages.

Galanthamine and acid addition salts thereof have, for many years, been known to have anticholinesterase properties.

Galanthamine, a tertiary alkaloid, has been isolated form the bulbs of the Caucasian snowdrops Galantanus woronowi (Proskurnina, N.F. and Vakoleva, A.P. 1952, Alkaloids of Galanthus woronowi. II. Isolation of a new alkaloid. (In Russian.) Zh. Obschchei Khim. (J. Gen. Checm.) 22, 1899–1902. Chem.abs. 47,6969, 1953. It has also been isolated from the common snowdrop Galanthus Nivalis (Boit, 1954).

Galanthamine has been used extensively as a curare reversal agent in anaesthetic practice in Eastern bloc countries (cf. review by Paskow, 1986) and also experimentally in the West (of. Bretagne and Valetta, 1965: Wislicki, 1967; Conzanitis, 1971).

Pharmacokinetic studies have recently been made by Thomsen, T. and H. Kewitz. (Selective Inhibition of Human Acetyl- cholinesterase by Galanthamine in vitro and in vivo. Life Sciences, Vol 46, pp. 1553–1558 (1990), and, by the same authors, Galanthamine Hydrobromide in Long-Term Treatment of Alzheimer's Disease. Dementia 1990, 1:46–51).

It is believed that the excellent and surprising effect possessed by galanthamine is due to its specific profile of properties, the most important of the known ones of which can be summarized as follows:

capability to pass the blood brain barrier in humans, a high selectivity for acetylcholinesterase as opposed to butyrylcholinesterase (about 50-fold when measured by the in vitro method by Thomsen et al., see below), a sufficient elimination half life to warrant duration of an effective concentration of at least 4 hours, probably at least 6 hours, a relatively low toxicity in therapeutical concentrations, capability of being effective in doses which are sufficiently low to keep peripheral side effects low.

Galanthamine must be considered as being a very desirable drug for the treatment according to the invention: The elimination half life of galanthamine hydrobromide is over four hours; it shows a practically complete renal elimination. A complete elimination of metabolites and galanthamine takes place in 72 hours. Galanthamine has been used in Eastern Bloc countries since around 1958 as anticurare agent in anesthesiology, and a considerably number of patients have been treated with galanthamine without any reported case of liver toxicity or serious side effects. Galanthamine hydrobromide, being a tertiary amino and lipid soluble, is absorbed rapidly from the gut and transverses the blood brain barrier easily. The common side effects, other than the ones related to cholinergic crisis, are either nausea or vomiting, and a slight headache. However, these side effects are rare, especially when care is taken to start medication in low doses such as mentioned above.

The galanthamine can suitably be administered orally in the form of an acid addition salt, e.g. the hydrobromide, but other administration forms are possible and realistic, such as is described below.

Because galanthamine has substantially no affect on the activity at muscarinic receptor sites, as apparent from its high selectivity for acetylcholinesterase as opposed to butyrylcholinesterase, it will not give rise to the often severe side effects on the heart which are associated with cholinesterase inhibitors which have a low selectivity for acetylcholinesterase as opposed to butyrylcholinesterase. Galanthamine has an in vitro selectivity for acetylcholinesterase opposed the effect on butyrylcholinesterase of 50 to 1, as reported by Thomsen, Life Sciences, Vol 46, pp. 1553–1558 (1990).

As indicated above, the amount of galanthamine is preferably adjusted individually based upon observation of the effect of initially very low dosages. There is as considerable differences with respect to how sensitive individuals are to acetylcholinesterase inhibitors. Thus, the amount of galanthamine is suitably adjusted by means of a regimen starting at low dosages, e.g. 1 mg, preferably at 5 mg, per day, but, if appropriate, even as low as 0.1 mg per day, if the dosage is well tolerated by the patient within the first two hours the dosages is increased to, e.g. 10 mg per dosage dosed 3 to 4 times per day or in some severe cases to 60 mg or more per day dosed over 3 or 4 times.

Because cholinergic crisis, a life-threatening dose-dependant side effect of all kinds of acetylcholinesterase inhibitors, should, by all means, be avoided, it is recommended to start with the low dosages as mentioned above and furthermore not to exceed 150 mg per day and preferably not to exceed dosages above 60 mg per day, unless the patient shows a very low sensitivity to acetylcholinesterase inhibitor, in which case higher doses, such as 200 mg per day, could be used.

The treatment according to the invention should preferably be continued until the treatment with benzodiazepine is discontinued.

While galanthamine has, indeed, given remarkable results, such as appears from the clinical cases given in the examples, it is justified to presume that other acetylcholinesterase inhibitors which are functional equivalents to galanthamine with respect to its combination of high selectivity with respect to nicotinic receptor sites and capability of passing the blood brain barrier in humans in vivo, will also show a useful combination of effect against the sedative or hypnotic effects of benzodiazepines and acceptability in the clinic, although it cannot be ruled out that galanthamine, galanthamine salts and galanthamine derivatives, due to the special conformation of the galanthamine ring system, have specific properties which are decisive for the remarkable effect.

In accordance with the above, compounds which are functional equivalents of galanthamine are defined herein as compounds which a) possess an at least 10-fold selectivity, preferably an at least 20-fold selectivity, more preferably an at least 40-fold selectivity, and most preferably an at least 50 fold selectivity, for acetylcholinesterase as opposed to butyrylcholinesterase, when measured by the in vitro method by Thomsen et al., see below, b) are capable of passing the blood brain barrier in humans in vivo.

As will be understood from the above definition, a compound can be subjected to well-defined and relatively short-lasting tests (see below) to determine whether it fulfills criterion a) above. Then, the likelihood whether the compound will pass the blood brain barrier in humans in vivo (criterion b)) can be assessed in a model. One such model is a whole rat brain model in which rats are given the acetylcholine esterase in vivo and are then killed whereupon homogenate of the rat brain is examined with respect to the acetylcholinesterase activity; the result is then compared to the acetylcholinesterase activity in rat brains not treated with acetylcholinesterase inhibitors. Another rat model could be the measurement and comparison of acetylcholinesterase activity in cerebrospinal fluid in vivo in the same rat before and after treatment. If the compound fulfills criterion a), and its likelihood of passing the blood brain barrier has been established in one of the above-described rat brain models, it will be a candidate drug. An initial determination of toxicity is necessary in cases before any effect in humans can be assessed; such initial determination of toxicity can be performed by pharmacologic tests in a manner known per se. After the pharmacological tests, the capability of the candidate drug of passing the blood brain barrier in humans in vivo can be determined by the method described below. If the candidate drug has been found to possess this capability, it can be passed to the testing proper. Optionally, the candidate drug can be subjected to additional short-lasting tests, such as the in vivo selectivity test described by Thomsen et al., and a test to determine whether it increases cortisol level in humans. Both of these tests give further indication of whether the candidate drug has a spectrum of properties equivalent to galanthamine with respect to what must be presumed to be essential properties. Peripheral side effects will be assessable when the effect is tested clinically, which is acceptable from an experimental and ethical point of view, provided the toxicity has first been assessed by the above-mentioned pharmacological tests. With respect to the final assessment of the candidate drug's effect on the sedative or hypnotic effects of benzodiazepines, a rational and efficient design of the assessment will involve an initial test on one or a few patients and, provided the initial test is positive, the above-mentioned conclusive double blind test. Because of the well-defined and brief character of all of the tests, and especially the well-defined in vitro character of the initial screening, the test series for identifying useful functional equivalents of galanthamine is a reasonable an not burdensome routine which is within the realm of the person skilled in the art.

Functional equivalents and derivatives of galanthamine which are useful in the method of the invention will be employed in the same manner as stated herein for galanthamine. Whenever quantities of such a functional equivalent or derivative are referred to herein, the quantities are given as the equipotent quantity of galanthamine hydrobromide with respect to inhibition of acetylcholinesterase, that is, as the quantity of galanthamine hydrobromids which results in the same inhibition of acetylcholine esterase in the above-mentioned in vitro test according to Thomsen et al as does the functional derivative or derivative.

The selectivity of the acetylcholinesterase inhibitor for acetylcholinesterase as opposed to butyrylcholinesterase can be determined by in vitro and in vivo tests as described by Thomsen and Kewitz in the above mentioned paper Selective Inhibition of Human Acetylcholinesterase by Galanthamine in vitro and in vivo, Life Sciences, Vol 46, pp. 1553–1558 (1990), and T. Thomsen, H. Kewitz and O. Plaul, J. Clin. Chem, Clin. Biochem. 26 469–475 (1988). The in vitro test described by Thomsen and Kewitz in Life Sciences, Vol 46, pp 1553–1558 (1990) is the one referred to above in connection with criterion a) and whenever numeric (10-fold, 20-fold, 40-fold) reference to selectivity for acetylcholinesterase as opposed to butyrylcholinesterase is made in the claims. According to Thomsen and Kewitz, galanthamine hydrobromide, when tested under the conditions described, shows a 50-fold selectivity; this selectivity value is taken as the "fixpoint" whenever in vitro selectivities are discussed herein and could be used, for the purpose of determining the selectivities for other cholinesterase inhibitors, as a calibration value which is the one to establish with galanthamine hydrobromide in any repetition of the experiment described by Thomsen and Kewitz. Thus, with reference to this determination method, a preferred acetylcholinesterase inhibitor is one which in the in vitro method described has an at least 10-fold selectivity for acetylcholinesterase as opposed to butyrylcholinesterase, such as an at least 20-fold selectivity for acetylcholinesterase as opposed to butyrylcholinesterase, e.g. an at least 40-fold selectivity for acetylcholinesterase as opposed to butyrylcholinesterase.

A relatively easy commercially available selectivity test which can be used as a practical tool in the screening of candidate drugs is the test described in Example 1 herein.

The capability to pass the blood brain barrier in vivo in humans can be assessed by either by a test which could be called "Auditory brain stem response" or by a test which is based on the measurement of CRH, ACTH and cortisol. The rationale behind these tests, and the way they are performed, is explained in the following:

The auditory brain stem response test is based on the observation that manic-depressive patients are hypersensitive to cholinergic influences, one manifestation hereof being hypersensitivity to auditory signals as assessed by the increase of amplitude of auditory evoked potentials in the nuclei of the auditory system in the brain stem, i.e. on the "brain side" of the blood brain barrier. This hypersensitivity manifests itself in a lower amplitude than in normal humans when the person is not treated with a cholinargic agent such as acetylcholinesterase inhibitor; and a very significantly increase of the amplitude when the person has received a cholinergic agent, provided, of course, that the cholinergic agent is able to pass the blood brain barrier and thus enter the nuclei of the auditory system in the brain stem. See also example 3.

The other test based on the measurement of CRH (corticotropic-hormone releasing hormone released from the hypothalamus in the brain, and which releases both ACTH from the adenohypophysis and cortisol from the adrenal medulla) and ACTH (corticotropic hormone, which releases cortisol from the adrenal medulla) is carried out by measuring the CRH, ACTH and cortisol concentration in the blood in healthy persons before and after medication with acetylcholinesterase. If the concentration of all three hormone are increased after medication or at least CRH and cortisol are increased it is proven that the acetylcholinesterase has effect in the central nervous system, and since it is an in vivo experiment it is further proven that the acetylcholinesterase has passed the blood brain barrier.

As mentioned above, the selectivity of the acetylcholinesterase inhibitor can, as an additional characterization, optionally be expressed with reference to the in vivo determinations performed by Thomsen and Kewitz on galanthamine and described in the above-mentioned paper Selective Inhibition of Human Acetylcholinesterase by Galanthamine in vitro and in vivo, Life Sciences, Vol 46, pp. 1553–1558 (1990). With reference to this determination, a preferred acetylcholinesterase inhibitor is one which, upon administration in an amount of 10 mg to a healthy adult, results in inhibition of at least 40% of the acetylcholinesterase activity in erythrocytes from the adult within about 2–5 minutes and no substantial inhibition of butyrylcholinesterase therein, such as an acetylcholinesterase inhibitor which, when administered in an amount of 10 mg to a healthy adult, results in inhibition of at least 50% of the acetylcholinesterase activity in erythrocytes from the adult within about 2–5 minutes. For galanthamine, Thomsen and Kewitz found 65% inhibition of acetylcholinesterase in the erythrocytes within 2 minutes after administration of 10 mg of galanthamine i.v. in a healthy volunteer, whereas no inhibition of butyrylcholinesterase in plasma was seen. Also these determinations are referred to in claims herein and should, in connection with the evaluation of the corresponding selectivities of candidate drugs different from galanthamine hydrobromide be considered the "calibration fixpoints" which will be established with galanthamine hydrobromide in any repetition of this experiment.

As mentioned above, it is possible that galanthamine, galanthamine salts and galanthamine derivatives, due to the special conformation of the galanthamine ring system, have specific properties which are decisive for the remarkable effect established according to the present invention. Thus, according to one aspect of the invention, compounds which are contemplated to be valuable and useful in the treatment according to the invention are the compounds having the formula I (formula I also represent galanthamine itself)

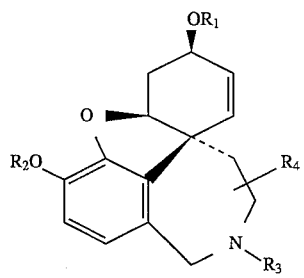

wherein $R^1$ and $R^2$ which may be the same or different each represents a hydrogen atom or an acyl group, such as a lower alkanoyl group, e.g. an acetyl group or a straightchained or branched alkyl group, e.g. methyl, ethyl, propyl, or isopropyl; $R^3$ is a straight or branched chain alkyl, alkenyl or alkaryl group which is optionally substituted by a halogen atom or a cycloalkyl, hydroxy, alkoxy, nitro, amino, aminoalkyl, acylamino, heteroaryl, heteroaryl-alkyl, aroyl, aroylalkyl or cyano group; and $R^4$ represents a hydrogen or halogen atom attached to at least one of the ring carbons of the tetracyclic skeleton, with the proviso that when $R^4$ is in a position neighbouring the nitrogen atom, then $R^4$ is preferably different from halogen, and salts thereof, such as a hydrobromide, hydrochloride, methylsulphate or methiodide.

In the compounds of formula I, alkyl moieties preferably contain 1 to 8 carbon atoms, halogen atoms are preferably fluorine, chlorine, or bromine, especially fluorine or chlorine, aryl moieties are preferably phenyl, cycloalkyl groups are preferably 3- to 7-membered rings, especially cyclopropyl or cyclobutyl, and heteroaryl moieties are preferably 5- to 8-membered rings, e.g., thienyl, furyl, pyridyl, pyrrolyl, or pyrizanyl.

Among the compounds of the formula I are those described in EP-A-236684. The compounds of formula I may be prepared according to conventional techniques, including those described in EP-A-236684.

A broader range of compounds which, from the point of view of structural similarity with galanthamine, are contemplated to be valuable compounds useful in the method of the invention are galanthamine derivatives of the general formula II

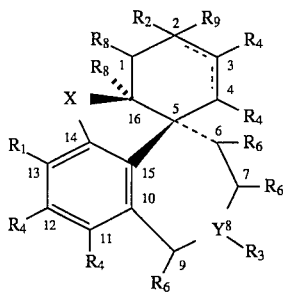

wherein the broken line represents an optionally present double bond in one or the two of the positions shown, $R_1$ and $R_2$ are each selected independently from the group consisting of hydrogen, hydroxyl, amino or alkylamino, cyano, sulfhydryl, alkoxy of 1–6 carbon atoms, alkylthio, aryloxy, arylthio, $R_5$-substituted aryloxy, $R_5$-substituted arylthio, aralkoxy, an aliphatic or aryl carbamyl group wherein the aliphatic or aryl moiety may be $R_5$ substituted or unsubstituted, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxycarbonyl and $R_5$-substituted aryloxycarbonyl, $R_1$ may also be alkyl of up to 14 carbon atoms, or hydroxymethyl, $R_2$ may also be carboxymethyl, provided that at least one of $R_1$ and $R_2$ is hydroxy, amino or alkylamino unless $R_8$ is hydroxymethyl, $R_3$ is hydrogen, straight or branched chain alkyl of 1–6 carbon atoms, cycloalkylmethyl, phenyl, $R_5$-substituted phenyl, alkylphenyl, $R_5$-substituted alkylphenyl, heterocyclyl selected from α- or β-furyl, α- or β-thienyl, thenyl, pyridyl, pyrazinyl, and pyrimidyl, alkylheterocyclyl or R'-substituted heterocyclyl, where R' is alkyl or alkoxy, each $R_4$ is independently selected from hydrogen, hydroxyl, sulfhydryl, alkyl, aryl, aralkyl, alkoxy, mercaptoalkyl, aryloxy, thiaryloxy, alkaryloxy, mercaptoalkaryl, nitro, amino, N-alkylamino, N-arylamino, N-alkarylamino, fluoro, chloro, bromo, iodo, and trifluoromethyl, $R_5$ is selected from the same groups as $R_4$, $R_6$ is hydrogen, halo, trifluoromethyl or alkyl of 1 to 4 carbon atoms, with the proviso that when $R^6$ is in position 7 or 9, it is preferably not halo.

$R_8$ is hydrogen or hydroxymethyl, $R_9$ is hydrogen or alkyl of 1 to 6 carbon atoms, or when $R_2$ is hydroxyl, $R_9$ may be a moiety of formula II wherein $R_9$ is hydrogen and $R_2$ is a linking bond; or $R_2$ and $R_9$ may jointly form semicarbazone, X is oxygen or $NR_5$, Y is nitrogen or phosphorus, and methylenedioxy derivatives thereof with the proviso that when X is O, $R_3$ is not methyl when $R_1$ is methoxy, $R_2$ is hydroxy, and all $R_4$ are hydrogen, or a pharmaceutically acceptable acid addition salt thereof.

Examples of subclasses and specific compounds of the formula II are given in WO 88/08708, which also discloses methods for preparing the compounds II.

Galanthamine, galanthamine salts, galanthamine derivatives and galanthamine functional equivalents, when suited therefor, may be administered orally at a dosage of e.g. 5–150 mg per day, such as 10–60 mg per day, e.g. 10–50 mg, such as 10–40 mg, per day, the dosage being adapted to the patient and the patient's response. As mentioned above, the treatment should often be started with a low dosage and then increased until the suitable dosage has been established. The dosage of galanthamine functional equivalents or galanthamine derivatives is expressed as the equipotent amount of galanthamine hydrobromide, the reference basis being the capability of inhibiting acetylcholinesterase in the Thomsen et al. in vitro test mentioned above.

Examples of parenteral administration ranges are 0.1–1000 mg per day, such as 5–1000 mg per day, e.g. 10–500 mg per day, including 50–300 mg per day; lower dosages are often preferred, such as 10–50 mg per day, e.g. 10–30 mg per day.

For the oral administration, galanthamine or a galanthamine salt or derivative or a functional equivalent may be formulated, for example, as an aqueous suspension or a solution in aqueous ethanol or as a solid composition such as a tablet or capsule. Suspensions or solutions for oral administration are typically of a concentration of 1–50 mg/ml, more commonly 5–40 mg/ml, for example, 10–40 mg/ml, typically 20–30 mg/ml of galanthamine. Divided doses into the range 0.5–5 mg/kg body weight per day are useful, in some situations divided doses in the range of 0,1–3 mg/kg body weight per day may also prove useful. Examples of dosages are up to 2000 mg per day, such as 0.1–2000 mg per day, or 5–2000 mg per day. Other ranges that should be mentioned are 100–600 mg per day or 10–500 mg per day, such as 10–50 or 10–30 mg per day. Typically, one might administer a dosage of 20–100 mg per day to a patient of a body weight of 40–100 kg, although in appropriate cases such dosages may prove useful for patients having a body weight outside this range. However, in other instances dosages of 50–300 mg per day to a patient of body weight of 40–100 kg may also be very useful. In other cases, dosages as low as 10 mg and as high as 200 mg may be appropriate for persons in this body weight range.

Galanthamine and its acid addition salts form crystals. They are generally only sparingly soluble in water at room temperature; therefore, injectable compositions are normally in the form of an aqueous suspension. If necessary, pharmaceutically-acceptable suspension aids may be employed. Typically, such a suspension will be employed at a concentration of 0.1–50 mg/ml, such as 1–50 mg/ml, more commonly 5–40 mg/ml, for example, 5–30 mg/ml or 10–40 mg/ml, such as 10–30 mg/ml, especially 20–30 mg/ml of galanthamine. As mentioned above, typical dosage rates when administering galanthamine by injection are the range 0.01–20 mg per day depending upon the patient. For example, divided doses in the range_0,5–5 mg/kg body weight per day may prove useful. Typically, one might administer a dosage of 5–50 mg per day to a patient of body weight of 40–100 kg, although in appropriate cases such dosages may prove useful for patients having a body weight outside this range. In other cases, dosages as low as 5 mg and as high as 200 mg per day may be appropriate for persons in this body weight range.

Galanthamine and its pharmaceutically acceptable acid addition salts, and its derivatives and functional equivalents, when suited therefor, may be administered by subcutaneous, intravanous or intramuscular injection.

The parenteral dosage rate of galanthamine can also be expressed by reference to the body weight of the patient; in this case, a normal dosage rate will often be 0.1 to 4 mg/kg body weight. Depot compositions will often deliver a dosage rate of 0.01 to 5.0 mg/kg per day.

In preparing tablets or capsules, standard tablet or capsule-making techniques may be employed. If desired, a pharmaceutically acceptable carrier such as starch or lactose may be used in preparing galanthamine or galanthamine equivalent tablets. Capsules may be prepared using soft gelatine as the encapsulating agent. If desired, such capsules may be in the form of sustained release capsules wherein the main capsule contains microcapsules of galanthamine or functional equivalents thereof which release the contents over a period of several hours thereby maintaining a constant level of galanthamine or its functional equivalent in the patient's blood.

The following specific formulations may find use according to the invention:

Tablets or capsules containing 0.1, 1, 2, 5, 10 and 25 mg galantahamine hydrobromide or functional equivalent to be taken four times a day, or a sustained-release preparation delivering an equivalent daily dose.

Liquid formulation for oral administration available in 5 mg/ml and 25 mg/ml concentration.

Other interesting administration forms of galanthamine and functional equivalents are suppositories, a slow-release plaster, and other depot compositions.

All of the above-mentioned administration forms are prepared in manners known per se.

Although galanthamine must be considered as having a high degree of safety, there have been certain side effects in a few of the patients treated. These have been slight nausea in about 30% of the cases (the nausea, however, disappearing after about one week of treatment), vomiting and dizziness in 5–10% of the patients (also disappearing after about one week of treatment in most cases), and more severe side effects in 4–6% of the patients. These more severe side effects must be considered acceptable in view of the effect of the drug; however, in patients who are suspected of developing arrhythmia, it should be considered to administer, e.g., atropine in combination with the treatment according to the invention.

As mentioned above, the cholinesterase inhibitors including galanthamine and the galanthamine salts and the galanthamine derivatives may be used together with a benzodiazepine either simultaneously or non-simultaneously. Also, the drugs may be used in situations where the sedative or hypnotic effects of benzodiazepines given has caused problems and the treatment with a cholinesterase inhibitor initiates after the onset of the benzodiazepine treatment. Even in situations where the benzodiazepine treatment has to be discontinued temporarily because of the undesirable effects the cholinesterase inhibitors may be administered to shorten the period where the undesirable effects dominate.

In situations where the cholinesterase inhibitor may be given simultaneously with a benzodiazepine a pharmaceutical composition comprising both the cholinesterase inhibitor and the benzodiazepine.

The administration forms for the cholinesterase inhibitors, galanthamine, the galanthamine salts and the galanthamine derivatives may be orally and parenterally. The administration being dependent on the patient's age and weight, and on the daily life of the patient as well as the severity of the disease.

Parenteral administration may comprise suitable injection, e.g., intravenous, intramuscular, subcutaneous, as well as transdermal or rectally administration or implantation of e.g. suitable delivery devices, such as a intrathetical device.

Formulations for parenteral use may be a solution or suspension, a plaster for transdermal application, or a suppository.

EXAMPLE 1

Test for cholinesterase activity in blood samples

Method

SIGMA DIAGNOSTICS® CHOLINESTERASE (PTC) kit, available from Sigma Diagnostics, can be used for determining the activity and selectivity of cholinesterase inhibitors. In the following, it is illustrated how the kit is used for the determination of the activity and selectivity of Nivalin (Galanthamine hydrobromide).

Reactions involved in the cholinesterase assay are as follows:

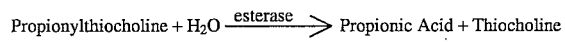

Thiocholine+5,5'-Dithiobis-2-Nitrobenzoic Acid→5-Thio-2-Nitrobenzoic Acid

5-Thio-2-Nitrobenzoic Acid is assessed by measuring the absorbance at 405 nm. The rate of change in absorbance at 405 nm is directly proportional to cholinesterase activity.

The activity of erythrocyte cholinesterase may be calculated on the basis of the measurement of butyrylcholinesterase (pseudocholinesterase) in serum and cholinesterase in hemolyzed whole blood (hemolysate), both measured simultaneously by the method described above, and evaluated according to the hematocrit value according to the formula $$HChE=(EChE \times Hct^*)+(PChE \times (1-Hct^*))$$

Therefore, $$EChE = \frac{HChE - (PChE \times (1 - Hct^*))}{Hct^*}$$

*Hematocrit value expressed as decimal equivalent (i.e., 44% = 0.44).

In the above formulae, EchE is erythrocyte cholinesterase activity, PChE is plasma cholinesterase activity, HChE is hemolysate cholinesterase activity, and Hct is hematocrit value of the sample.

Another way of assessing the cholinesterase activity is to measure the plasma cholinesterase and the cholinesterase in purified hemolyzed erythrocytes. By doing this, the values are obtained directly.

Blood samples from 3 patients were tested with the Sigma test. The tests were carried out with samples where no Nivalin was added and with samples where 1.25 µg/ml Nivalin and 2.5 µg/ml were added in vitro. The results are shown below in table 1.1.

TABLE 1.1

| Nivalin added µg/ml | Hemolysate ChE activity | Serum ChE activity |
|---|---|---|
| 0 | 1600 | 1900 |
| 1.25 | 0.96 | 0.98 |
| 2.50 | 0.86 | 0.97 |

The results show a significant reduction of the hemolysate cholinesterase activity with increased concentration of galanthamine hydrobromide, whereas the data for the serum activity do not show any statistically significant change as a response to the addition of the galanthamine hydrobromide, which is an indication of a high selectivity of the galanthamine hydrobromide with respect to acetylcholinesterase as opposed to butyrylcholinesterase. Selectivity for acetylcholinesterase in erythrocytes opposed to butyrylcholinesterase is contemplated to reflect the selectivity for acetylcholinesterase at nicotinic receptor sites opposed to the acetylcholinesterase at muscarinic receptor sites.

This test may be used as a screening for candidate cholinesterase inhibitors with respect to the selectivity.

EXAMPLE 2

Formulations of tablets containing galanthamine

| Composition of 1 tablet containing 1 mg galanthamine | |
|---|---|
| Galanthamine hydrobromide | 0.001 g |
| Calcium Phosphate | 0.032 g |
| Lactose | 0.005 g |
| Wheat Starch | 0.0056 g |
| Microcrystalline Cellulose | 0.015 g |
| Talc | 0.0007 g |
| Magnesium Stearate | 0.0007 g |
| Composition of 1 tablet containing 5 mg galanthamine | |
| Galanthamine hydrobromide | 0.005 g |
| Calcium phosphate | 0.024 g |
| Lactose | 0.004 g |
| Wheat Starch | 0.004 g |
| Microcrystalline Cellulose | 0.04 g |
| Talc | 0.002 g |
| Magnesium Stearate | 0.001 g |
| Composition of 1 tablet containing 10 mg galanthamine | |
| Galanthamine hydrobromide | 0.010 g |
| Lactose | 0.040 g |
| Wheat Starch | 0.0234 g |
| Microcrystalline Cellulose | 0.0374 g |
| Talc | 0.0036 g |
| Magnesium Stearate | 0.0012 g |
| Gelatin | 0.0044 g |

Preparation

All the tablets are prepared according to routine tabletting procedures.

EXAMPLE 3

Clinical trials of the effect of galanthamine counteracting the sedative or hypnotic effects of benzodiazepines.

Methods and materials

Drugs

Nivalin tablets containing 5 mg galanthamine, obtained from Waldheim Ltd., Vienna, Austria.

Rivotril tablets containing 0.5 mg clonasepam.

The following case examples are demonstrative of the effect of Nivalin on the sedative or hypnotic effects of benzodiazepines.

Case No. 1

A 40 year old man, a dentist, was admitted to the hospital suffering from an acute attack of panic reaction.

He was treated with 0.5 mg clonazepam tablets 3 times a day and at the same time 5 mg galanthamine hydrobromide tablets 3 times a day. Because of the combination treatment he was able to go home the same day and furthermore, able to continue his work as a dentist during 3 months of treatment. This would not have been the case if he had been treated with clonazepam alone.

Case No. 2

A female school teacher had a growing agoraphobia (fear for open places) and panic reactions and was abusing benzodiazepines.

She was treated with 5 mg clonasepam tablets 3 times a day and at the same time 0.5 mg galanthamine hydrobromide tablets 3 times a day. Due to the administration of the galanthamine hydrobromide, she could still function in her job despite her treatment with clonazepam.

These case stories show that the combination of benzodiazepines and galanthamine hydrobromide enables the patients to live a normal daily life despite of the fact that they are receiving 15 mg of clonazepam per day, a dose which, without the treatment with galanthamine hydrobromide, would have kept them in hospital for a long time.

EXAMPLE 4

Auditory brain stem response

Methods

Electrical potentials caused by click-stimulation in the ears are measured with electrodes positioned outside on the head of the examine person. In the configuration of the potentials are components from the brain stem and the brain.

Persons

A patient suffering from bipolar manic-depression in the depressive state and a healthy person, respectively.

Drug

Tablet containing 10 mg galanthamine

Results

Brief Description of the Drawings FIGS. 1A, 1B, 2A and 2B show the potentials from a depressive patient and a healthy person, both treated and untreated.

FIGS. 1A, and 2A show that in the depressed patient, the auditory brain stem response without treatment has a much smaller, almost half, amplitude of the potential compared to the amplitude of the untreated healthy person.

Furthermore, FIGS. 1A and 1B show a dramatically increase of the amplitude in the treated depressive patient compared to untreated persons.

Also, from FIGS. 2A and 2B it is seen that the potentials do not change from the untreated person to the treated person.

Conclusion

From the results in the depressed person it is seen that the potentials change after treatment with galanthamine, such as explained above. This means that galanthamine must be able to cross the blood-brain barrier, since it is possible to inhibit in synapsis in the brain stem, which is positioned on the "brain side" of the blood-brain barrier.

LEGENDS TO FIGURES

Figure 1A:
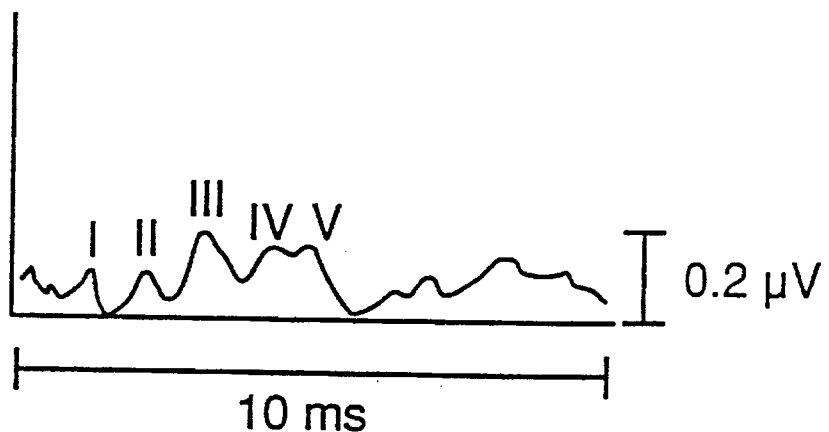
FIG. 1A shows the auditory evoked response of a depressed patient (a manic depressed patient in the depressed state) without treatment with galanthamine.
Figure 1B:
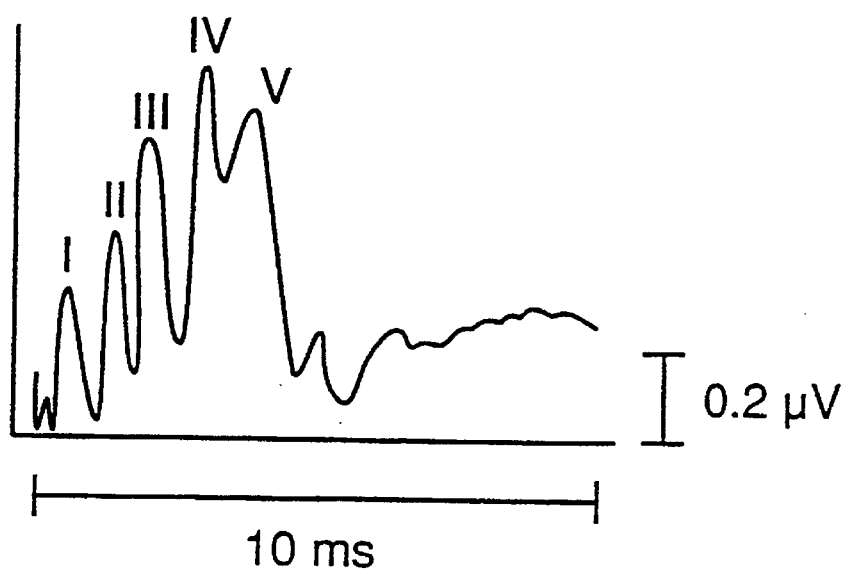
FIG. 1B shows the auditory evoked response of a depressed patient (the same as in FIG. 1A) 2 hours after treatment with 10 mg of galanthamine.
Figure 2A:
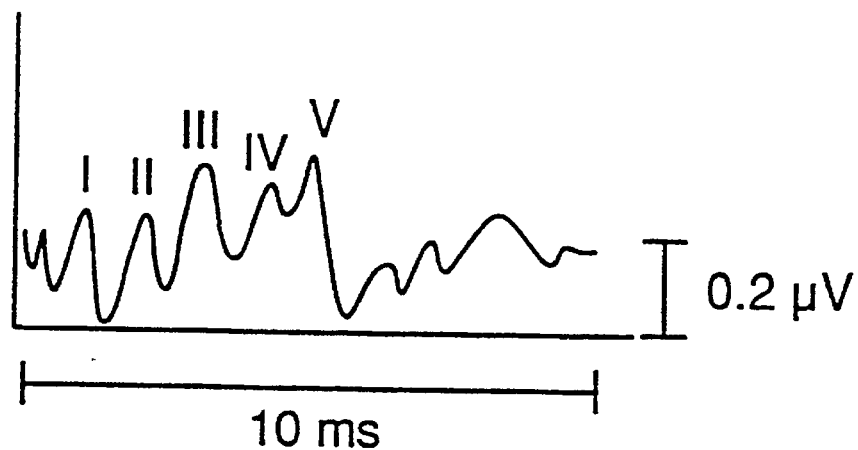
FIG. 2A shows the auditory evoked response of a healthy person without treatment with galanthamine.
Figure 2B:
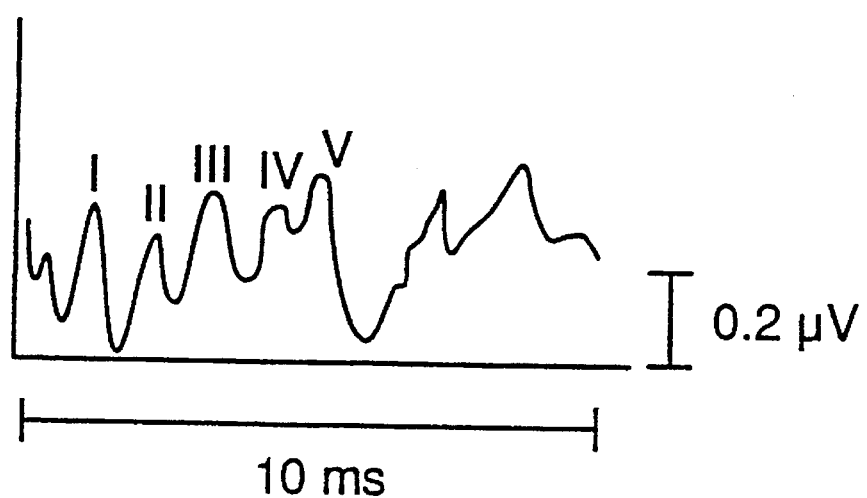
FIG. 2B shows the auditory evoked response of a healthy person (the same as in FIG. 2A) 2 hours after treatment with 10 mg of galanthamine.

I claim:

1. A method for counteracting the sedative, hypnotic or respiratory depressive effects of benzodiazepines, substantially without interfering with the anxiolytic, antipsychotic, anticonvulsant, and muscle relaxant activity of benzodiazepines, comprising the steps of administering, to a patient subjected to benzodiazepine therapy, an effective amount of galanthamine or a galanthamine derivative of the formula I

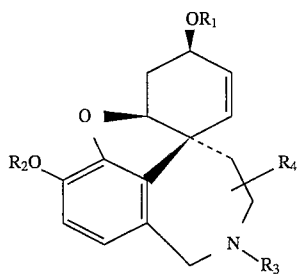

wherein $R^1$ and $R^2$ represents a hydrogen atom or an acyl group, and wherein $R^1$ and $R^2$ may be the same or different;

$R^3$ is a straight or branched chain alkyl, alkenyl or alkaryl group which is optionally substituted by a halogen atom or a cycloalkyl, hydroxy, alkoxy, nitro, amino, amino-alkyl, acylamino, heteroaryl, heteroaryl-alkyl, aroyl, aryolalkyl or cyano group; and $R^4$ represents a hydrogen or halogen atom attached to at least one of the ring carbons of the tetracyclic skeleton, with the proviso that when $R_4$ is in a position neighboring the nitrogen atom, then $R_4$ is not halogen;

or a pharmaceutically acceptable salt thereof.

2. The method of claim 1, wherein said acyl group of said galanthamine derivative, or salt thereof is a lower alkanoyl group.

3. The method of claim 2, wherein said lower alkanoyl group is an acetyl group or a straight-chained or branched alkyl group.

4. The method of claim 3, wherein said alkyl group is methyl, ethyl, propyl, or isopropyl.

5. The method of claim 1, wherein said pharmaceutically acceptable salt is a hydrobromide, hydrochloride, methylsulphate or methiodide.

6. A method for counteracting the sedative, hypnotic or respiratory depressive effects of benzodiazepines, substantially without interfering with the anxiolytic, antipsychotic, anticonvulsant, and muscle relaxant activity of benzodiazepines, comprising the steps of administering, to a patient subjected to benzodiazepine therapy, an effective amount of a galanthamine derivative of the general formula, II:

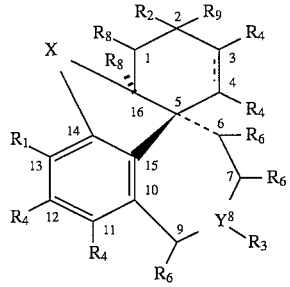

wherein the bond represented by the broken line between the carbon atoms at positions 3 and 4 represents an optionally present double bond, $R_1$ and $R_2$ are each selected independently from the group consisting of hydrogen, hydroxyl, amino or alkylamino, cyano, sulfhydryl, alkoxy of 1–6 carbon atoms, alkylthio, aryloxy, arylthio, $R_5$-substituted aryloxy, $R_5$-substituted arylthio, aralkoxy, an aliphatic or aryl carbamyl group wherein the aliphatic or aryl moiety may be $R_5$ substituted or unsubstituted, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxycarbonyl and $R_5$-substituted aryloxycarbonyl, $R_1$ may also be alkyl of up to 14 carbon atoms, or hydroxymethyl, $R_2$ may also be carboxymethyl, provided that at least one of $R_1$ and $R_2$ is hydroxy, amino or alkylamino, unless $R_8$ is hydroxymethyl, $R_3$ is hydrogen, straight or branched chain alkyl of 1–6 carbon atoms, cycloalkylmethyl, phenyl, $R_5$-substituted phenyl, alkylphenyl, $R_5$-substituted alkylphenyl, heterocyclyl selected from α- or β-furyl, α- or β-thienyl or thenyl, pyridyl, pyrazinyl, and pyrimidyl, alkyl-heterocyclyl or R'-substituted heterocyclyl, wherein R' is alkyl or alkoxy, each $R_4$ is independently selected from hydrogen, hydroxyl, sulfhydryl, alkyl, aryl, aralkyl, alkoxy, mercaptoalkyl, aryloxy, thiaryloxy, alkaryloxy, mercarptoalkaryl, nitro, amino, N-alkylamino, N-arylamino, N-alkarylamino, fluoro, chloro, bromo, iodo, and trifluoromethyl, $R_5$ is selected from the same group as $R_4$, $R_6$ is hydrogen, a halogen, trifluoromethyl or alkyl of 1 to 4 carbon atoms, with the proviso that when $R_6$ is in position 7 or 9, it is not a halogen, $R_8$ is hydrogen or hydroxymethyl, $R_9$ is hydrogen or alkyl of 1 to 6 carbon atoms, or when $R_2$ is hydroxyl, $R_9$ may be a moiety of formula II wherein $R_9$ may jointly form semicarbazone, X is oxygen or $NR_5$, Y is nitrogen or phosphorus, and methylenedioxy derivatives thereof, with the proviso that when X is O, $R_3$ is not methyl, when $R_1$ is methoxyl, $R_2$ is hydroxyl, and all $R_4$ are hydrogen, or a pharmaceutically acceptable acid addition salt thereof.

7. The method of claim 5, wherein said pharmaceutically acceptable salt is galanthamine hydrobromide.

8. The method according to claim 1, wherein said benzodiazepine is being used for treatment of a disease or condition wherein the sedative, hypnotic or respiratory depressive effects of said benzodiazepine are undesirable.

9. The method according to claim 1, wherein said benzodiazepine is being used for treatment of a disease or condition selected from the group consisting of anxiety, anxiety neurosis, anxiety reactions, panic reactions, schizophrenia, affective or schizoaffective type schizophrenia, borderline psychosis, agitated endogenous depressions, hyperactivity in children, and muscle spasms.

10. The method according to claim 1, wherein said galanthamine, galanthamine derivative, or salt thereof is administered in the form of a tablet, a capsule, a sustained release capsule comprising micro capsules of said galanthamine, galanthamine derivative, or salt thereof, a solution, a suspension, a plaster, or a suppository.

11. The method according to claim 1, wherein said galanthamine, galanthamine derivative, or salt thereof is administered at a dosage which is equipotent with 0.1–1,000 mg of galanthamine hydrobromide per day.

12. The method according to claim 1, wherein said galanthamine, galanthamine derivative, or salt thereof is administered at a dosage which is equipotent with 5–500 mg of galanthamine hydrobromide per day.

13. The method according to claim 12, wherein said galanthamine, galanthamine derivative, or salt thereof is provided in a dosage which is equipotent with 10–500 mg of galanthamine hydrobromide per day.

14. The method according to claim 12, wherein said galanthamine, galanthamine derivative, or salt thereof is provided in a dosage which is equipotent with 50–300 mg of galanthamine hydrobromide per day.

15. The method of claim 13, wherein said dosage is equipotent with 10–50 mg galanthamine hydrobromide per day.

16. The method of claim 13, wherein said dosage is equipotent with 10–30 mg galanthamine hydrobromide per day.

17. The method according to claim 1, wherein said galanthamine, galanthamine derivative, or salt thereof is administered orally at a dosage which is equipotent with 0.1–2000 mg galanthamine hydrobromide per day.

18. The method according to claim 1, wherein said galanthamine, galanthamine derivative, or salt thereof is administered orally at a dosage which is equipotent with 5–2,000 mg galanthamine hydrobromide per day.

19. The method according to claim 18, wherein said dosage is equipotent with 10–500 mg galanthamine hydrobromide per day.

20. The method according to claim 18, wherein said dosage is equipotent with 10–50 mg galanthamine hydrobromide per day.

21. The method according to claim 18, wherein said dosage is equipotent with 10–30 mg galanthamine hydrobromide per day.

22. A kit for treating a patient with a benzodiazepine whereby sedative, hypnotic and/or respiratory depressive effects are counteracted substantially without interfering with the anxiolytic, antipsychotic, anticonvulsant, and muscle relaxant activity of benzodiazepines, said kit comprising a package containing a unit dosage of a galanthamine or a galanthamine derivative of the formula I

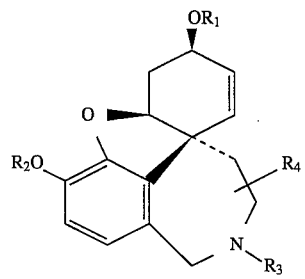

wherein $R^1$ and $R^2$ represents a hydrogen atom or an acyl group, and wherein $R^1$ and $R^2$ may be the same or different; p1 $R^3$ is a straight or branched chain alkyl, alkenyl or alkaryl group which is optionally substituted by a halogen atom or a cycloalkyl, hydroxy, alkoxy, nitro, amino, amino-alkyl, acylamino, heteroaryl, heteroaryl-alkyl, aroyl, aryolalkyl or cyano group; and $R^4$ represents a hydrogen or halogen atom attached to at least one of the ring carbons of the tetracyclic skeleton, with the proviso that when $R_4$ is in a position neighboring the nitrogen atom, then $R_4$ is not a halogen;

or a pharmaceutically acceptable salt thereof, and a package containing a unit dosage of a benzodiazepine.

23. The kit of claim 22, wherein said galanthamine or a galanthamine derivative, or salt thereof is provided in more than one unit dosage, and wherein said benzodiazepine is provided in more than one unit dosage.

24. The kit of claim 22, wherein said unit dosages of a galanthamine or a galanthamine derivative, or salt thereof and said unit dosages of a benzodiazepine are equipotent with one another.

25. A method for counteracting the sedative, hypnotic or respiratory depressive effects of benzodiazepines, substantially without interfering with anxiolytic, antipsychotic, anticonvulsant and muscle relaxant activity of benzodiazepines comprising administering to a patient in need thereof, an effective amount of galanthamine, a galanthamine salt or a galanthamine derivative.

26. The method of claim 25, wherein said patient receives a galanthamine derivative of the formula I

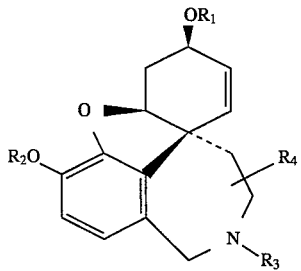

wherein $R^1$ and $R^2$ represents a hydrogen atom or an acyl group, and wherein $R^1$ and $R^2$ may be the same or different;

$R^3$ is a straight or branched chain alkyl, alkenyl or alkaryl group which is optionally substituted by a halogen atom or a cycloalkyl, hydroxy, alkoxy, nitro, amino, amino-alkyl, acylamino, heteroaryl, heteroaryl-alkyl, aryl, aryolalkyl or cyano group; and $R^4$ represents a hydrogen or halogen atom attached to at least one of the ring carbons of the tetracyclic skeleton, with the proviso that when $R_4$ is in a position neighboring the nitrogen atom, then $R_4$ is not a halogen;

or a pharmaceutically acceptable salt thereof.

27. The method of claim 25, wherein said patient receives a galanthamine derivative of formula II

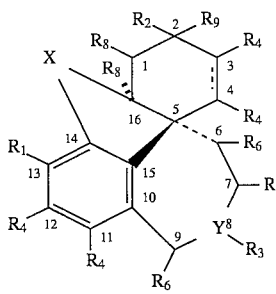

wherein the bond represented by the broken line between carbon atoms 3 and 4 represents an optionally present double bond, $R_1$ and $R_2$ are each selected independently from the group consisting of hydrogen, hydroxyl, amino or alkylamino, cyano, sulfhydryl, alkoxy of 1–6 carbon atoms, alkylthio, aryloxy, arylthio, $R_5$-substituted aryloxy, $R_5$-substituted arylthio, aralkoxy, an aliphatic or aryl carbamyl group wherein the aliphatic or aryl moiety may be $R_5$ substituted or unsubstituted, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxycarbonyl and $R_5$-substituted aryloxycarbonyl, $R_1$ may also be alkyl of up to 14 carbon atoms, or hydroxymethyl, $R_2$ may also be carboxymethyl, provided that at least one of $R_1$ and $R_2$ is hydroxy, amino or alkylamino, unless $R_8$ is hydroxymethyl, $R_3$ is hydrogen, straight or branched chain alkyl of 1–6 carbon atoms, cycloalkylmethyl, phenyl, $R_5$-substituted phenyl, alkylphenyl, $R_5$-substituted alkylphenyl, heterocyclyl selected from α- or β-furyl, α- or β-thienyl or thenyl, pyridyl, pyrazinyl, and pyrimidyl, alkylheterocyclyl or R'-substituted heterocyclyl, wherein R' is alkyl or alkoxy, each $R_4$ is independently selected from hydrogen, hydroxyl, sulfhydryl, alkyl, aryl, aralkyl, alkoxy, mercaptoalkyl, aryloxy, thiaryloxy, alkaryloxy, mercarptoalkaryl, nitro, amino, N-alkylamino, N-arylamino, N-alkarylamino, fluoro, chloro, bromo, iodo, and trifluoromethyl, $R_5$ is selected from the same group as $R_4$, $R_6$ is hydrogen, a halogen, trifluoromethyl or alkyl of 1 to 4 carbon atoms, with the proviso that when $R_6$ is in position 7 or 9, it is not a halogen, $R_8$ is hydrogen or hydroxymethyl, $R_9$ is hydrogen or alkyl of 1 to 6 carbon atoms, or when $R_2$ is hydroxyl, $R_9$ may be a moiety of formula II wherein $R_9$ may jointly form semicarbazone, X is oxygen or $NR_5$, Y is nitrogen or phosphorus, and methylenedioxy derivatives thereof, with the proviso that when X is O, $R_3$ is not methyl, when $R_1$ is methoxyl, $R_2$ is hydroxyl, and all $R_4$ are hydrogen, or a pharmaceutically acceptable acid addition salt thereof.

28. The method according to claim 6, wherein said benzodiazepine is being used for treatment of a disease or condition wherein the sedative, hypnotic or respiratory depressive effects of said benzodiazepine are undesirable.

29. The method according to claim 6, wherein said benzodiazepine is being used for treatment of a disease or condition selected from the group consisting of anxiety, anxiety neurosis, anxiety reactions, panic reactions, schizophrenia, affective or schizoaffective type schizophrenia, borderline psychosis, agitated endogenous depressions, hyperactivity in children, and muscle spasms.

30. The method according to claim 6, wherein said galanthamine derivative, or salt thereof, is administered in the form of a tablet, a capsule, a sustained release capsule comprising micro capsules of said galanthamine derivative or salt thereof, a solution, a suspension, a plaster, or suppository.

31. The method according to claim 6, wherein said galanthamine derivative, or salt thereof, is administered at a dosage which is equipotent with 0.1–1,000 mg of galanthamine hydrobromide per day.

32. The method according to claim 6, wherein said galanthamine derivative, or salt thereof, is administered at a dosage which is equipotent with 5–500 mg of galanthamine hydrobromide per day.

33. The method according to claim 32, wherein said galanthamine derivative, or salt thereof, is provided in a dosage which is equipotent with 10–500 mg of galanthamine hydrobromide per day.

34. The method according to claim 32, wherein said galanthamine derivative, or salt thereof, is provided in a dosage which is equipotent with 50–300 mg of galanthamine hydrobromide per day.

35. The method according to claim 6, wherein said galanthamine derivative, or salt thereof, is administered orally at a dosage which is equipotent with 0.1–2000 mg galanthamine hydrobromide per day.

36. The method according to claim 6, wherein said galanthamine derivative, or salt thereof, is administered orally at a dosage which is equipotent with 5–2,000 mg galanthamine hydrobromide per day.

37. A kit for treating a patient with a benzodiazepine whereby sedative, hypnotic and/or respiratory depressive effects are counteracted substantially without interfering with the anxiolytic, antipsychotic, anticonvulsant, and muscle relaxant activity of benzodiazepines, said kit comprising a package containing a unit dosage of a galanthamine derivative of the formula II

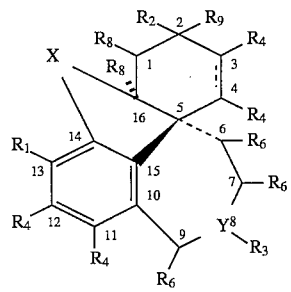

wherein the bond represented by the broken line between carbon atoms 3 and 4 represents an optionally present double bond, $R_1$ and $R_2$ are each selected independently from the group consisting of hydrogen, hydroxyl, amino or alkylamino, cyano, sulfhydryl, alkoxy of 1–6 carbon atoms, alkylthio, aryloxy, arylthio, $R_5$-substituted aryloxy, $R_5$-substituted arylthio, aralkoxy, an aliphatic or aryl carbamyl group wherein the aliphatic or aryl moiety may be $R_5$ substituted or unsubstituted, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxycarbonyl and $R_5$-substituted aryloxycarbonyl, $R_1$ may also be alkyl of up to 14 carbon atoms, or hydroxymethyl, $R_2$ may also be carboxymethyl, provided that at least one of $R_1$ and $R_2$ is hydroxy, amino or alkylamino, unless $R_8$ is hydroxymethyl, $R_3$ is hydrogen, straight or branched chain alkyl of 1–6 carbon atoms, cycloalkylmethyl, phenyl, $R_5$-substituted phenyl, alkylphenyl, $R_5$-substituted alkylphenyl, heterocyclyl selected from α- or β-furyl, α- or β-thienyl or thenyl, pyridyl, pyrazinyl, and pyrimidyl, alkylheterocyclyl or R'-substituted heterocyclyl, wherein R' is alkyl or alkoxy, each $R_4$ is independently selected from hydrogen, hydroxyl, sulfhydryl, alkyl, aryl, aralkyl, alkoxy, mercaptoalkyl, aryloxy, thiaryloxy, alkaryloxy, mercarptoalkaryl, nitro, amino N-alkylamino, N-arylamino, N-alkarylamino, fluoro, chloro, bromo, iodo, and trifluoromethyl, $R_5$ is selected from the same group as $R_4$, $R_6$ is hydrogen, a halogen, trifluoromethyl or alkyl of 1 to 4 carbon atoms, with the proviso that when $R_6$ is in position 7 or 9, it is not a halogen, $R_8$ is hydrogen or hydroxymethyl, $R_9$ is hydrogen or alkyl of 1 to 6 carbon atoms, or when $R_2$ is hydroxyl, $R_9$ may be a moiety of formula II wherein $R_9$ may jointly form semicarbazone, X is oxygen of $NR_5$, Y is nitrogen or phosphorus, and methylenedioxy derivatives thereof, with the proviso that when X is O, $R_3$ is not methyl, when $R_1$ is methoxyl, $R_2$ is hydroxyl, and all $R_4$ are hydrogen, or a pharmaceutically acceptable acid addition salt thereof, and a package containing a unit dosage of a benzodiazepine.

38. The kit of claim 37, wherein said galanthamine derivative, or salt thereof, is provided in more than one unit dosage, and wherein said benzodiazepine is provided in more than one unit dosage.

39. The kit of claim 37, wherein said unit dosages of said galanthamine derivative, or salt thereof, and said unit dosages of a benzodiazepine are equipotent with one another.

40. The method of claim 1, wherein said galanthamine or galanthamine derivative, or salt thereof, is able to cross the blood-brain barrier.

41. The method of claim 6, wherein said galanthamine or galanthamine derivative, or salt thereof, is able to cross the blood-brain barrier.

42. A method for counteracting the sedative, hypnotic or respiratory depressive effects of benzodiazepines, substantially without interfering with the anxiolytic, antipsychotic, anticonvulsant, and muscle relaxant activity of benzodiazepines, comprising the steps of administering, to a patient subjected to benzodiazepine therapy, an effective amount of epigalanthamine or norgalanthamine.

* * * * *